US008033995B2

(12) United States Patent  
Cropper et al.

(10) Patent No.: US 8,033,995 B2
(45) Date of Patent: Oct. 11, 2011

(54) INFLATABLE RETRACTOR WITH INSUFFLATION AND METHOD

(75) Inventors: Michael S. Cropper, Edgewood, KY (US); Gregory W. Johnson, Milford, OH (US); Kevin L. Houser, Springdale, OH (US); William Bruce Weisenburgh, II, Maineville, OH (US); Frederick E. Shelton, IV, Hillsboro, OH (US); Christopher J. Hess, Cincinnati, OH (US); Denzel Z. Herrera-Davis, Cincinnati, OH (US); Jerome R. Morgan, Cincinnnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 182 days.

(21) Appl. No.: 12/479,398

(22) Filed: Jun. 5, 2009

(65) Prior Publication Data

US 2010/0312066 A1 Dec. 9, 2010

(51) Int. Cl.
*A61B 1/32* (2006.01)
(52) U.S. Cl. ...................................................... 600/207
(58) Field of Classification Search .................... 600/31, 600/115, 116, 201, 206, 207, 470
See application file for complete search history.

(56) References Cited

U.S. PATENT DOCUMENTS

| | | | |
|---|---|---|---|
| 2,129,391 A | 9/1938 | Wappler | |
| 3,402,710 A | 9/1968 | Paleschuck | |
| 3,654,965 A | 4/1972 | Gramain | |
| 4,112,932 A | 9/1978 | Chiulli | |
| 4,306,545 A | 12/1981 | Ivan et al. | |
| 4,379,458 A | 4/1983 | Bauer et al. | |
| 4,402,683 A | 9/1983 | Kopman | |
| 4,417,888 A | 11/1983 | Cosentino et al. | |
| 5,010,925 A | 4/1991 | Atkinson et al. | |
| 5,091,435 A | 2/1992 | Suzuki et al. | |
| 5,183,471 A | 2/1993 | Wilk | |

(Continued)

FOREIGN PATENT DOCUMENTS

DE 19814576 A1 10/1999

(Continued)

OTHER PUBLICATIONS

International Search Report and Written Opinion for International App. No. PCT/US2010/036811 dated Sep. 14, 2010 (6 pages).
International Search Report, from PCT/US10/36829, mailed Sep. 9, 2010 (5 pages).
European Search Report, EP 10250732, dated Jul. 28, 2010.

(Continued)

*Primary Examiner* — John J Wilson
(74) *Attorney, Agent, or Firm* — Nutter McClennen & Fish LLP (57) ABSTRACT

Various methods and devices are provided for accessing a body cavity. In one embodiment, a surgical access device is provided and includes an elongate member having a proximal support member configured to rest against an external tissue surface, a flexible elongate central portion extending distally from the proximal support member and configured to extend through tissue, and an inflatable distal portion coupled to a distal end of the central portion. The distal portion is movable between an initial configuration, in which the distal portion is configured to be passed through an incision in tissue, and an inflated configuration in which the distal portion is expanded such that the central portion forms a working channel through the tissue for access to a body cavity. The distal portion can include an opening such that gas delivered to the distal portion can flow through the opening to insufflate a body cavity.

20 Claims, 11 Drawing Sheets

U.S. PATENT DOCUMENTS

| | | | |
|---|---|---|---|
| 5,197,955 A | 3/1993 | Stephens et al. |
| 5,207,213 A | 5/1993 | Auhll et al. |
| 5,209,737 A | 5/1993 | Ritchart et al. |
| 5,209,741 A | 5/1993 | Spaeth |
| 5,235,966 A | 8/1993 | Jamner |
| 5,269,772 A | 12/1993 | Wilk |
| 5,308,336 A | 5/1994 | Hart et al. |
| 5,312,417 A | 5/1994 | Wilk |
| 5,320,611 A | 6/1994 | Bonutti et al. |
| 5,342,315 A | 8/1994 | Rowe et al. |
| 5,366,478 A | 11/1994 | Brinkerhoff et al. |
| 5,385,553 A | 1/1995 | Hart et al. |
| 5,385,560 A | 1/1995 | Wulf |
| 5,391,154 A | 2/1995 | Young |
| 5,431,676 A | 7/1995 | Dubrul et al. |
| 5,443,452 A | 8/1995 | Hart et al. |
| 5,443,484 A | 8/1995 | Kirsch et al. |
| 5,476,475 A | 12/1995 | Gadberry |
| 5,480,410 A | 1/1996 | Cuschieri et al. |
| 5,531,758 A | 7/1996 | Uschold et al. |
| 5,545,179 A | 8/1996 | Williamson, IV |
| 5,562,677 A | 10/1996 | Hildwein et al. |
| 5,569,205 A | 10/1996 | Hart et al. |
| 5,569,254 A | 10/1996 | Carlson et al. |
| 5,584,850 A | 12/1996 | Hart et al. |
| 5,628,732 A | 5/1997 | Antoon, Jr. et al. |
| 5,634,911 A | 6/1997 | Hermann et al. |
| 5,634,937 A | 6/1997 | Mollenauer et al. |
| 5,643,301 A | 7/1997 | Mollenauer |
| 5,653,705 A | 8/1997 | de la Torre et al. |
| 5,653,718 A | 8/1997 | Yoon |
| 5,672,168 A | 9/1997 | de la Torre et al. |
| 5,676,657 A | 10/1997 | Yoon |
| 5,695,448 A | 12/1997 | Kimura et al. |
| 5,707,359 A | 1/1998 | Bufalini |
| 5,752,970 A | 5/1998 | Yoon |
| 5,782,812 A | 7/1998 | Hart et al. |
| 5,797,888 A | 8/1998 | Yoon |
| 5,803,919 A | 9/1998 | Hart et al. |
| 5,814,058 A | 9/1998 | Carlson et al. |
| 5,827,319 A | 10/1998 | Carlson et al. |
| 5,843,040 A | 12/1998 | Exline |
| 5,865,807 A | 2/1999 | Blake, III |
| 5,868,762 A | 2/1999 | Cragg et al. |
| 5,882,344 A | 3/1999 | Stouder, Jr. |
| 5,891,013 A | 4/1999 | Thompson |
| 5,899,208 A | 5/1999 | Bonadio |
| 5,906,577 A | 5/1999 | Beane et al. |
| 5,946,280 A | 8/1999 | Ohkubo |
| 5,957,913 A | 9/1999 | de la Torre et al. |
| 5,990,382 A | 11/1999 | Fox |
| 5,997,515 A | 12/1999 | de la Torre et al. |
| 6,024,736 A | 2/2000 | de la Torre et al. |
| 6,033,428 A * | 3/2000 | Sardella ................ 606/213 |
| RE36,702 E | 5/2000 | Green et al. |
| 6,056,766 A | 5/2000 | Thompson et al. |
| 6,066,090 A | 5/2000 | Yoon |
| 6,077,288 A | 6/2000 | Shimomura et al. |
| 6,080,174 A | 6/2000 | Dubrul et al. |
| 6,086,603 A | 7/2000 | Termin et al. |
| 6,102,928 A * | 8/2000 | Bonutti ................ 606/190 |
| 6,120,513 A | 9/2000 | Bailey et al. |
| 6,123,689 A | 9/2000 | To et al. |
| 6,142,396 A | 11/2000 | Gallus |
| 6,142,936 A | 11/2000 | Beane et al. |
| 6,162,196 A | 12/2000 | Hart et al. |
| 6,217,555 B1 | 4/2001 | Hart et al. |
| 6,245,052 B1 | 6/2001 | Orth et al. |
| 6,258,069 B1 | 7/2001 | Carpentier et al. |
| 6,277,064 B1 | 8/2001 | Yoon |
| 6,315,770 B1 | 11/2001 | de la Torre et al. |
| 6,319,246 B1 | 11/2001 | de la Torre et al. |
| 6,325,812 B1 | 12/2001 | Dubrul et al. |
| 6,348,034 B1 | 2/2002 | Thompson |
| 6,352,503 B1 | 3/2002 | Matsui et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,458,077 B1 | 10/2002 | Boebel et al. |
| 6,488,620 B1 | 12/2002 | Segermark et al. |
| 6,551,270 B1 | 4/2003 | Bimbo et al. |
| 6,551,282 B1 | 4/2003 | Exline et al. |
| 6,589,167 B1 | 7/2003 | Shimomura et al. |
| 6,605,063 B2 | 8/2003 | Bousquet |
| 6,669,674 B1 | 12/2003 | Macoviak et al. |
| 6,702,787 B2 | 3/2004 | Racenet et al. |
| 6,706,033 B1 | 3/2004 | Martinez et al. |
| 6,706,050 B1 | 3/2004 | Giannadakis |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 7,014,628 B2 | 3/2006 | Bousquet |
| 7,052,454 B2 | 5/2006 | Taylor |
| 7,083,626 B2 | 8/2006 | Hart et al. |
| 7,118,528 B1 | 10/2006 | Piskun |
| 7,163,510 B2 | 1/2007 | Kahle et al. |
| 7,163,525 B2 | 1/2007 | Franer |
| 7,214,185 B1 | 5/2007 | Rosney et al. |
| 7,229,408 B2 | 6/2007 | Douglas et al. |
| 7,338,473 B2 | 3/2008 | Campbell et al. |
| 7,344,547 B2 | 3/2008 | Piskun |
| 7,371,227 B2 | 5/2008 | Zeiner |
| 7,393,322 B2 | 7/2008 | Wenchell |
| 7,449,011 B2 | 11/2008 | Wenchell et al. |
| 7,481,795 B2 | 1/2009 | Thompson et al. |
| 2002/0156432 A1 | 10/2002 | Racenet et al. |
| 2003/0028179 A1 | 2/2003 | Piskun |
| 2003/0139756 A1 | 7/2003 | Brustad |
| 2003/0216770 A1 | 11/2003 | Persidsky et al. |
| 2004/0015185 A1 | 1/2004 | Ewers et al. |
| 2004/0019322 A1 | 1/2004 | Hoffmann |
| 2004/0082969 A1 | 4/2004 | Kerr |
| 2004/0106942 A1 | 6/2004 | Taylor et al. |
| 2004/0117032 A1 | 6/2004 | Roth |
| 2004/0138528 A1 | 7/2004 | Richter et al. |
| 2004/0199121 A1 | 10/2004 | Wenchell et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0182286 A1* | 8/2005 | Lubock ...................... 600/3 |
| 2005/0192483 A1 | 9/2005 | Bonadio et al. |
| 2005/0209608 A1 | 9/2005 | O'Heeron |
| 2005/0215862 A1 | 9/2005 | Larson et al. |
| 2005/0216028 A1 | 9/2005 | Hart et al. |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0012965 A1 | 1/2006 | Beall et al. |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0021061 A1 | 1/2006 | Cerri et al. |
| 2006/0021891 A1 | 2/2006 | Franer et al. |
| 2006/0025813 A1 | 2/2006 | Shelton et al. |
| 2006/0030755 A1 | 2/2006 | Ewers et al. |
| 2006/0071432 A1 | 4/2006 | Staudner |
| 2006/0129165 A1 | 6/2006 | Edoga et al. |
| 2006/0212061 A1 | 9/2006 | Wenchell |
| 2006/0212062 A1 | 9/2006 | Farascioni |
| 2006/0217665 A1 | 9/2006 | Prosek |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247498 A1 | 11/2006 | Bonadio et al. |

| | | | |
|---|---|---|---|
| 2006/0247500 A1 | 11/2006 | Voegele et al. | |
| 2006/0247516 A1 | 11/2006 | Hess et al. | |
| 2006/0247586 A1 | 11/2006 | Voegele et al. | |
| 2006/0247673 A1 | 11/2006 | Voegele et al. | |
| 2006/0247678 A1 | 11/2006 | Weisenburgh et al. | |
| 2006/0258899 A1 | 11/2006 | Gill et al. | |
| 2006/0264706 A1 | 11/2006 | Piskun | |
| 2006/0270911 A1 | 11/2006 | Voegele et al. | |
| 2007/0049966 A1 | 3/2007 | Bonadio et al. | |
| 2007/0060939 A1 | 3/2007 | Lancial et al. | |
| 2007/0085232 A1 | 4/2007 | Brustad et al. | |
| 2007/0088202 A1 | 4/2007 | Albrecht et al. | |
| 2007/0088204 A1 | 4/2007 | Albrecht et al. | |
| 2007/0088258 A1 | 4/2007 | Wenchell et al. | |
| 2007/0088277 A1 | 4/2007 | McGinley et al. | |
| 2007/0118021 A1 | 5/2007 | Pokorney | |
| 2007/0118175 A1 | 5/2007 | Butler et al. | |
| 2007/0151566 A1 | 7/2007 | Kahle et al. | |
| 2007/0185453 A1 | 8/2007 | Michael et al. | |
| 2007/0208312 A1 | 9/2007 | Norton et al. | |
| 2007/0255219 A1 | 11/2007 | Vaugh et al. | |
| 2008/0009797 A1 | 1/2008 | Stellon et al. | |
| 2008/0025519 A1 | 1/2008 | Yu et al. | |
| 2008/0027476 A1 | 1/2008 | Piskun | |
| 2008/0051739 A1 | 2/2008 | McFarlane | |
| 2008/0058728 A1 | 3/2008 | Soltz et al. | |
| 2008/0065021 A1 | 3/2008 | Jenkins et al. | |
| 2008/0086080 A1 | 4/2008 | Mastri et al. | |
| 2008/0119821 A1 | 5/2008 | Agnihotri et al. | |
| 2008/0132765 A1 | 6/2008 | Beckman et al. | |
| 2008/0255519 A1 | 10/2008 | Piskun et al. | |
| 2008/0281161 A1 | 11/2008 | Albrecht et al. | |
| 2009/0005799 A1 | 1/2009 | Franer et al. | |
| 2009/0082731 A2 | 3/2009 | Moreno | |
| 2009/0105543 A1* | 4/2009 | Miller et al. | 600/155 |
| 2009/0118587 A1 | 5/2009 | Voegele et al. | |
| 2009/0187079 A1 | 7/2009 | Albrecht et al. | |
| 2009/0270685 A1 | 10/2009 | Moreno et al. | |
| 2009/0270686 A1 | 10/2009 | Duke et al. | |
| 2009/0270818 A1 | 10/2009 | Duke | |
| 2009/0299137 A1* | 12/2009 | Gal et al. | 600/109 |
| 2010/0010310 A1 | 1/2010 | Weisenburgh, II et al. | |
| 2010/0081863 A1 | 4/2010 | Hess et al. | |
| 2010/0081864 A1 | 4/2010 | Hess et al. | |
| 2010/0081871 A1 | 4/2010 | Widenhouse et al. | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0228090 A1 | 9/2010 | Weisenburgh, II et al. | |
| 2010/0228091 A1 | 9/2010 | Widenhouse et al. | |
| 2010/0228092 A1 | 9/2010 | Ortiz et al. | |
| 2010/0228094 A1 | 9/2010 | Ortiz et al. | |
| 2010/0228096 A1 | 9/2010 | Weisenburgh, II et al. | |
| 2010/0228198 A1 | 9/2010 | Widenhouse et al. | |
| 2010/0249525 A1 | 9/2010 | Shelton, IV et al. | |
| 2010/0261970 A1 | 10/2010 | Shelton, IV et al. | |
| 2010/0261972 A1 | 10/2010 | Widenhouse et al. | |
| 2010/0261974 A1 | 10/2010 | Shelton, IV et al. | |
| 2010/0262080 A1 | 10/2010 | Shelton, IV et al. | |
| 2010/0268162 A1 | 10/2010 | Shelton, IV et al. | |
| 2010/0274093 A1 | 10/2010 | Shelton, IV | |
| 2010/0280327 A1 | 11/2010 | Nobis et al. | |
| 2010/0312060 A1 | 12/2010 | Widenhouse et al. | |
| 2010/0312061 A1 | 12/2010 | Hess et al. | |
| 2010/0312062 A1 | 12/2010 | Cropper et al. | |
| 2010/0312063 A1 | 12/2010 | Hess et al. | |
| 2010/0312064 A1 | 12/2010 | Weisenburgh, II et al. | |
| 2010/0312065 A1 | 12/2010 | Shelton, IV et al. | |
| 2010/0312066 A1 | 12/2010 | Cropper et al. | |
| 2010/0312189 A1 | 12/2010 | Shelton, IV et al. | |

FOREIGN PATENT DOCUMENTS

| | | |
|---|---|---|
| DE | 20022005 U1 | 4/2001 |
| EP | 0568383 | 11/1993 |
| EP | 568383 A1 | 11/1993 |
| EP | 577400 A1 | 1/1994 |
| EP | 0637431 A1 | 2/1995 |
| EP | 0646358 | 4/1995 |
| EP | 646358 A1 | 4/1995 |
| EP | 709918 | 5/1996 |
| EP | 0776231 B1 | 6/1997 |
| EP | 950376 | 10/1999 |
| EP | 1219251 A1 | 7/2002 |
| EP | 1219252 A1 | 7/2002 |
| EP | 1219253 A1 | 7/2002 |
| EP | 1350476 | 10/2003 |
| EP | 1702575 A2 | 9/2006 |
| EP | 1731105 A1 | 12/2006 |
| EP | 1774918 A1 | 4/2007 |
| EP | 2119404 A1 | 11/2009 |
| FR | 2710270 | 3/1995 |
| FR | 2710270 | 3/1995 |
| JP | 2006320750 | 11/2006 |
| WO | 9407552 A1 | 4/1994 |
| WO | 9602297 A1 | 2/1996 |
| WO | 9608897 A1 | 3/1996 |
| WO | 9636283 A1 | 11/1996 |
| WO | 9743958 A1 | 11/1997 |
| WO | 0032263 A1 | 6/2000 |
| WO | 0041759 A1 | 7/2000 |
| WO | 0108563 A2 | 2/2001 |
| WO | 0217800 A2 | 3/2002 |
| WO | 2004030515 A2 | 4/2004 |
| WO | 2005000454 A1 | 1/2005 |
| WO | 2005002454 A1 | 1/2005 |
| WO | 2005087112 A1 | 9/2005 |
| WO | 2005094432 A2 | 10/2005 |
| WO | 2005097019 A2 | 10/2005 |
| WO | 2005097234 A2 | 10/2005 |
| WO | 2006057982 A2 | 6/2006 |
| WO | 2007008741 A1 | 1/2007 |
| WO | 2007119232 A2 | 10/2007 |
| WO | 2008024502 A2 | 2/2008 |
| WO | 2008028149 A2 | 3/2008 |
| WO | 2008121294 A1 | 10/2008 |
| WO | 2009035663 A2 | 3/2009 |

OTHER PUBLICATIONS

International Search Report and Written Opinion for Application No. PCT/US2010/037190, dated Sep. 22, 2010 (15 pages).

"Surgeon performs single-port laparoscopic surgery > Kidney removal with instructions inserted through single port access SPA > One Port Umbilicus Surgery OPUS > Uretero-pelvic junction repair > Bilateral pyeloplasy > Triport > Quadport > R-Port laparoscopic access device > Advanced Surgical Concepts ASC" Ideas for Surgery.com, Dec. 2007, 4 pages.

Desai, Mihir M. et al., "Laparoscopic and Robtic Urology-Scarless single port transumbilical nephrectomy and pyeloplasty: first clinical report," Journal Compilation, 2008 BJU International, 101, pp. 83-88.

Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.

Nakajima K, et al. Hand-assisted laparoscopic colorectal surgery using GelPort, Surg Endosc. Jan. 2004; 18(1)102-5. Epub Sep. 10, 2003.

Nakajima K, et al. Use of the surgical towel in colorectal hand-assisted laparoscopic surgery (HALS), Surg Endosc. Mar. 2004; 18(3):552-3.

Patel, R. et al. "Hand-Assisted Laparoscopic Devices: The Second Generation," Journal of Endourology, vol. 18, No. 7, Sep. 2004, pp. 649-653.

Rane, A. et al., "Single-Port Access Nephrectomy and Other Laparoscopic Urologic Procedures Using a Novel Laparoscopic Port (R-Port)," Urology, Aug. 2008; 72(2):260-264.

International Search Report and Written Opinion for Application No. PCT/US2010/036806, dated Sep. 3, 2010 (8 pages).

International Search Report and Written Opinion for Application No. PCT/US2010/036820, dated Oct. 22, 2010 (18 pages).

* cited by examiner

INFLATABLE RETRACTOR WITH INSUFFLATION AND METHOD

FIELD OF THE INVENTION

The present invention relates to methods and devices for providing access into a body cavity, and more particularly to a retractor with an inflatable distal portion that can provide insufflation.

BACKGROUND OF THE INVENTION

Access ports are widely used in medical procedures to gain access to anatomical cavities ranging in size from the abdomen to small blood vessels, such as veins and arteries, epidural, pleural and subarachnoid spaces, heart ventricles, and spinal and synovial cavities. The use of access ports has become more common as they provide minimally invasive techniques for establishing a portal for a number of procedures, such as those involving the abdominal cavity.

Many of these types of procedures involve insufflation of the abdominal cavity with CO2 gas to increase interior space for a surgical procedure. This is often achieved using an additional port to allow gas to be passed into a body cavity to provide pressure therein to maintain insufflation of the cavity. One challenge facing surgeons when using these access ports is achieving initial insertion of the access ports through tissue and into a body cavity, especially in the case of an access port that is flexible. This can be made even more difficult before the body cavity is inflated as there are organs and other vital structures that can be directly adjacent the puncture site where the access port is inserted through the tissue and it is necessary to prevent damage to these organs during insertion of the ports.

Accordingly, there is a need for improved methods and devices for providing access into a body cavity.

SUMMARY OF THE INVENTION

The present invention provides various methods and devices for accessing a body cavity. In one embodiment, a surgical access device is provided and includes an elongate member having a working channel extending therethrough between a proximal end and a distal end. The elongate member can include a proximal support member configured to rest against an external tissue surface, a flexible elongate central portion extending distally from the proximal support member and configured to extend through tissue, and an inflatable distal portion coupled to a distal end of the central portion. The inflatable distal portion is movable between an initial configuration, in which the inflatable distal portion is configured to be passed through an incision in tissue, and an inflated configuration in which the inflatable distal portion is expanded such that the central portion forms a working channel through the tissue to provide access to a body cavity. The inflatable distal portion can include one or more openings formed therein such that gas delivered to the inflatable distal portion to move the inflatable distal portion to the inflated position flows through the at least one opening to allow insufflation of a body cavity containing the inflatable distal portion. The proximal support member can also include an insufflation port formed therein and in fluid communication with the inflatable distal portion of the elongate member. In one embodiment, the proximal support member and the inflatable distal portion can be ring-shaped.

The surgical access device can also include various other features, for example, to provide a seal through the device. In one embodiment, a membrane can extend across the distal end of the working channel and it can be effective to seal the working channel to allow insufflation of a body cavity during inflation of the inflatable distal portion. The membrane can have various features, but in one embodiment the membrane can be perforated such that insertion of a surgical instrument through the membrane is configured to tear the membrane along the perforations. The membrane can be perforated in a variety of ways, including along a substantial portion of a perimeter thereof. The membrane can also have various configurations. For example, a portion of the membrane can extend through the flexible elongate central portion. The membrane can be semi-rigid such that the membrane is configured to protect the flexible elongate central portion from being punctured by a surgical instrument. The surgical access device can also include a seal housing removably mated to the proximal support member. The seal housing can include at least one seal element disposed therein and configured to seal the working channel.

In another embodiment, a surgical access device is provided and includes a retractor having a proximal housing configured to rest adjacent an external tissue surface and a flexible member extending therefrom. The retractor can have a working channel extending therethrough and configured to form a working channel through tissue. The flexible member can include an inflatable portion having at least one opening formed therein. An insufflation port can be formed in the proximal housing and it can be in fluid communication with the inflatable portion such that the insufflation port is configured to deliver an insufflation gas to the inflatable portion of the flexible member to inflate the inflatable portion and to insufflate a body cavity through the openings formed in the inflatable portion.

The surgical access device can also include a puncturable membrane extending across the working channel such that the membrane is configured to be pushed through tissue to position the flexible member of the retractor through the tissue. In one embodiment, the membrane can be perforated along at least a portion of a perimeter thereof such that insertion of a surgical instrument through the working channel of the retractor is effective separate the membrane from the retractor along the perforations. In another embodiment, the surgical access device can include a seal housing removably mated to the proximal housing. The seal housing can include at least one seal element disposed therein and configured to seal the working channel.

Methods for accessing a body cavity are also provided, and in one embodiment the method can include positioning a proximal support of a surgical access device adjacent to a tissue surface, and inserting a flexible retractor of the access device through an incision in the tissue to position an inflatable portion of the flexible retractor within a body cavity. In one embodiment, inserting the flexible retractor through an incision in the tissue can include applying force to a flexible membrane extending across the working channel to insert the flexible retractor through the incision and to position the inflatable portion within the body cavity. The flexible membrane can seal the working channel of the access device to prevent escape of insufflation gas from the body cavity The method can also include delivering an insufflation gas to an insufflation port on the proximal support to inflate the inflatable portion such that a working channel of the access device forms a pathway through the tissue for introducing surgical instruments into the body cavity. The insufflation gas delivered to the inflatable portion can flow through at least one opening in the inflatable portion to insufflate the body cavity.

In one embodiment, the method can include coupling a seal housing to the proximal support of the surgical access device. The seal housing can have at least one seal element disposed therein that seals the working channel of the access device. The method can also further include inserting a surgical instrument through the seal element in the seal housing and into the body cavity such that the surgical instrument punctures the flexible membrane. In one embodiment, the flexible membrane can prevent contact between the flexible retractor and the surgical instrument.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for accessing a body cavity using a surgical access device, as illustrated in FIGS. 1-6. The surgical access device 10 generally includes a retractor 12 having a proximal support member 14 configured to rest against an external tissue surface, a flexible elongate central portion 16 extending distally from the proximal support member 14 and configured to extend through tissue, and an inflatable distal portion 18 coupled to a distal end 16d of the central portion 16. In general, the inflatable distal portion 18 of the retractor 12 is movable between an initial configuration in which the inflatable distal portion 18 is configured to be passed through an incision in tissue, and an inflated configuration in which the inflatable distal portion 18 is expanded such that the central portion 16 forms a working channel through the tissue to provide access to a body cavity. The inflatable distal portion 18 can also include at least one opening 20 formed therein. This allows the body cavity to be insufflated as a gas is delivered to the inflatable distal portion 18 to move the inflatable distal portion 18 to the inflated configuration. As will be discussed in more detail below, the surgical access device 10 can also optionally include a seal housing 22 with one or more sealing elements disposed therein and configured to seal the working channel.

Figure 1:
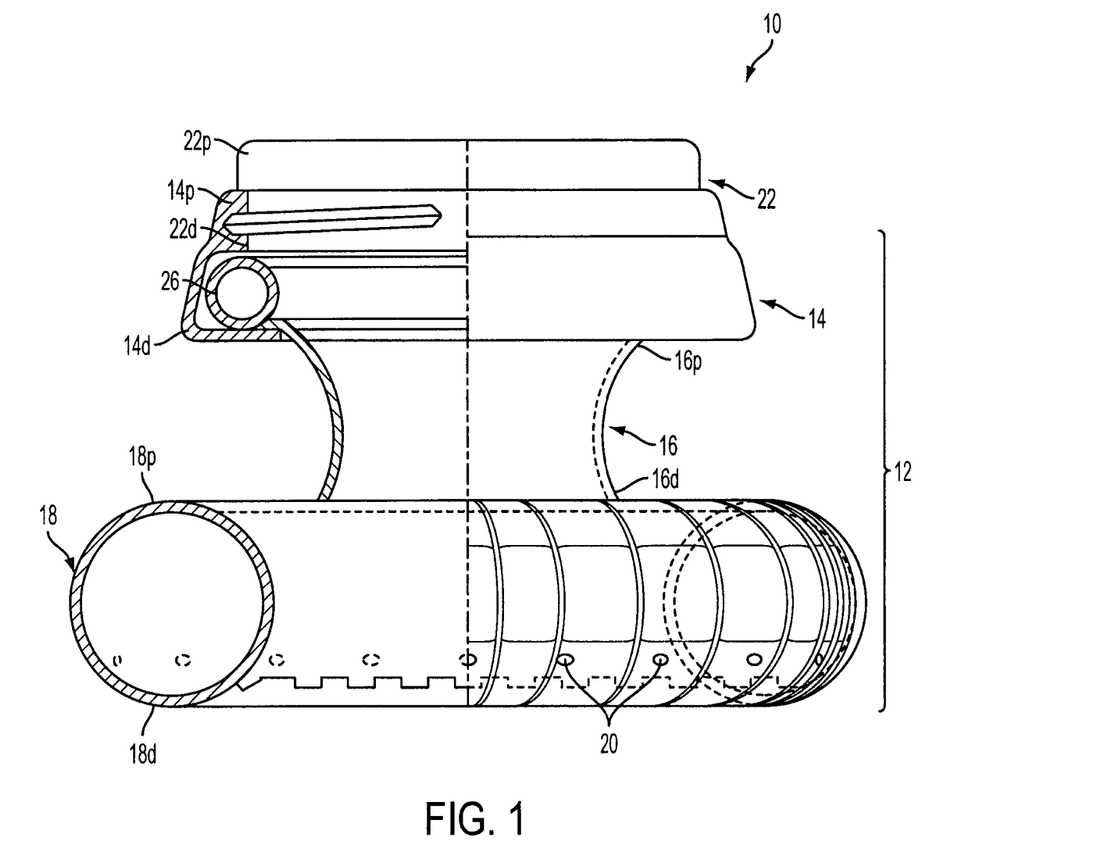
FIG. 1 is a side view of a surgical access device that includes a retractor having a proximal support portion and an elongate central portion extending therefrom with an inflatable distal portion, and a seal housing coupled to the proximal support portion of the retractor.
Figure 2:
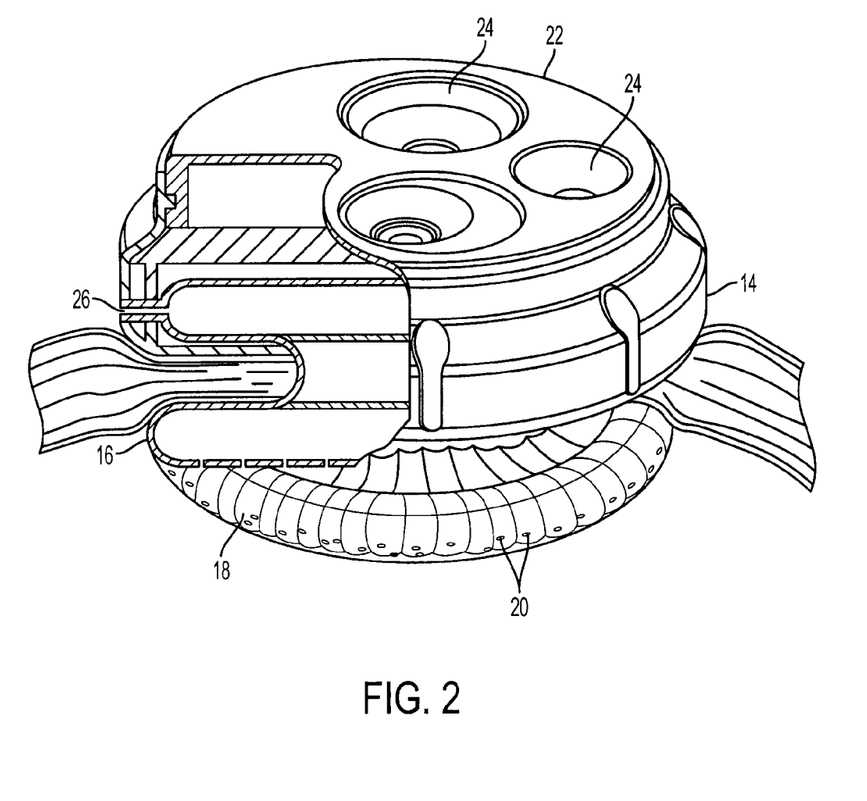
FIG. 2 is a perspective partial-cross sectional view of the surgical access device of FIG. 1.
Figure 3:
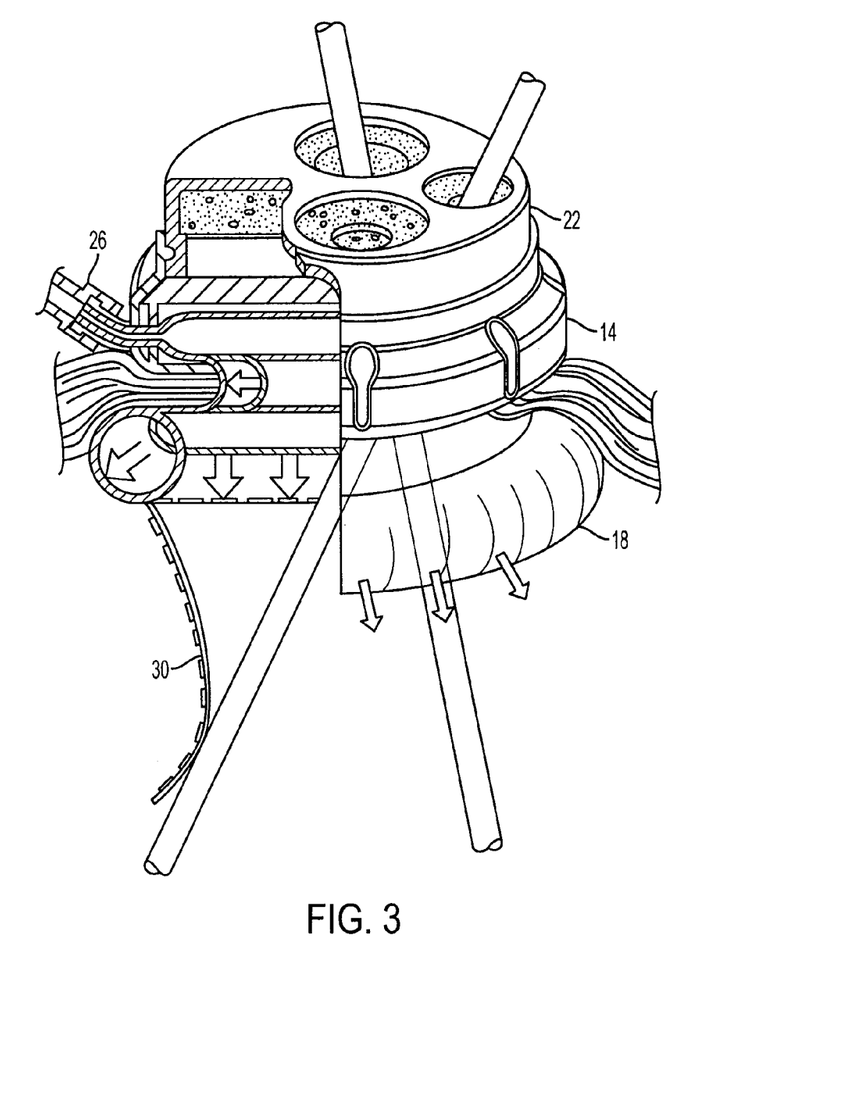
FIG. 3 is a perspective partial-cross-sectional view of the surgical access device of FIG. 1 having a membrane disposed across an inflatable distal portion of the retractor, with the membrane torn to open the working channel formed therethrough.
Figure 4:
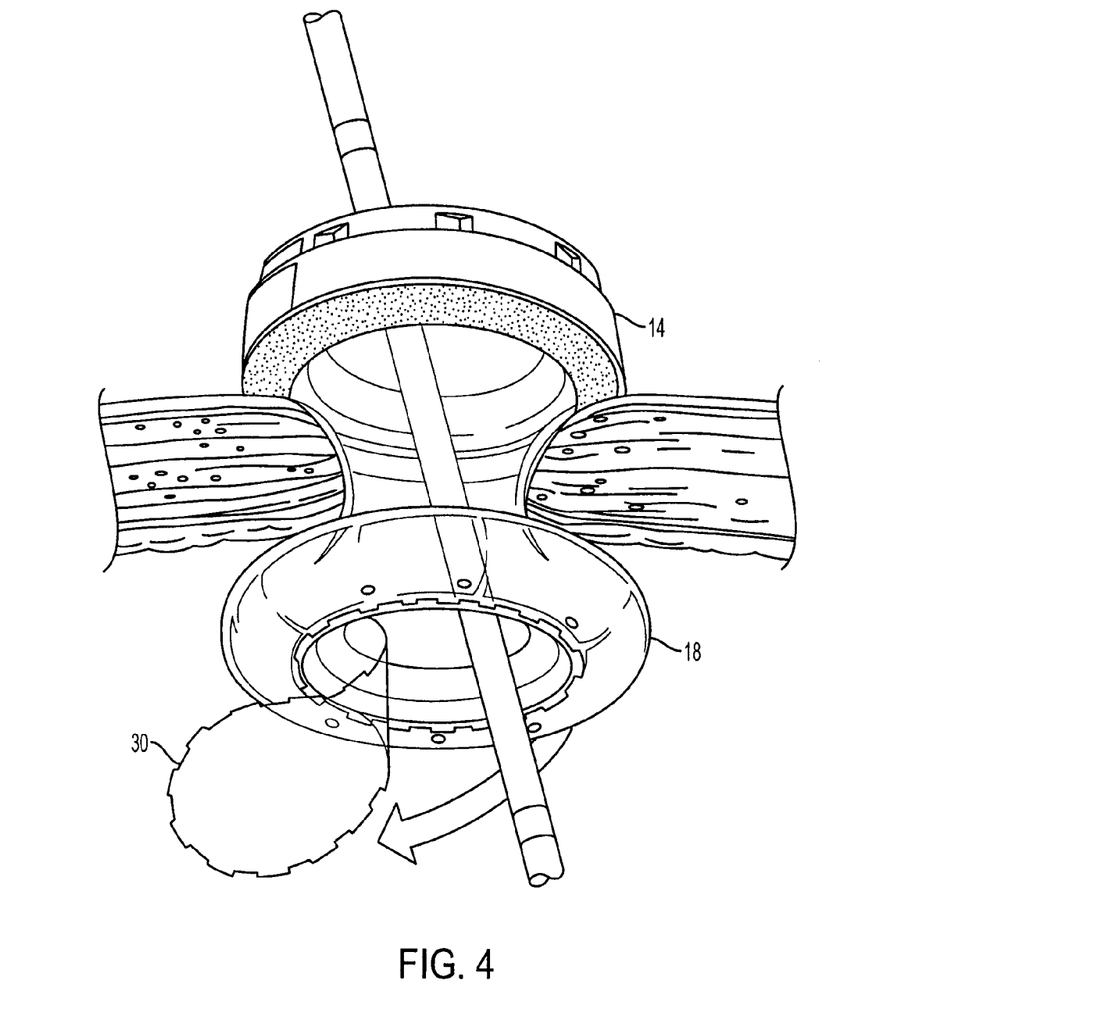
FIG. 4 is a perspective partial-cross-sectional view of the surgical access device of FIG. 3.
Figure 5:
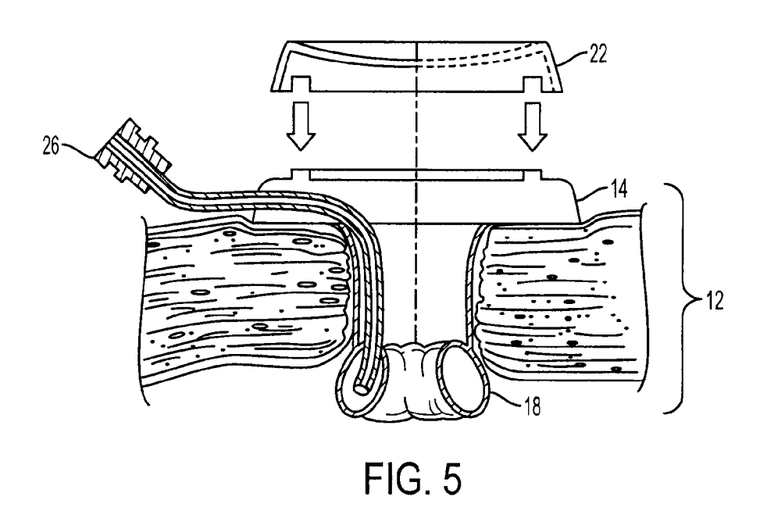
FIG. 5 is a side view of the surgical access device of FIG. 1 showing the inflatable distal portion in an initial, uninflated configuration.
Figure 6:
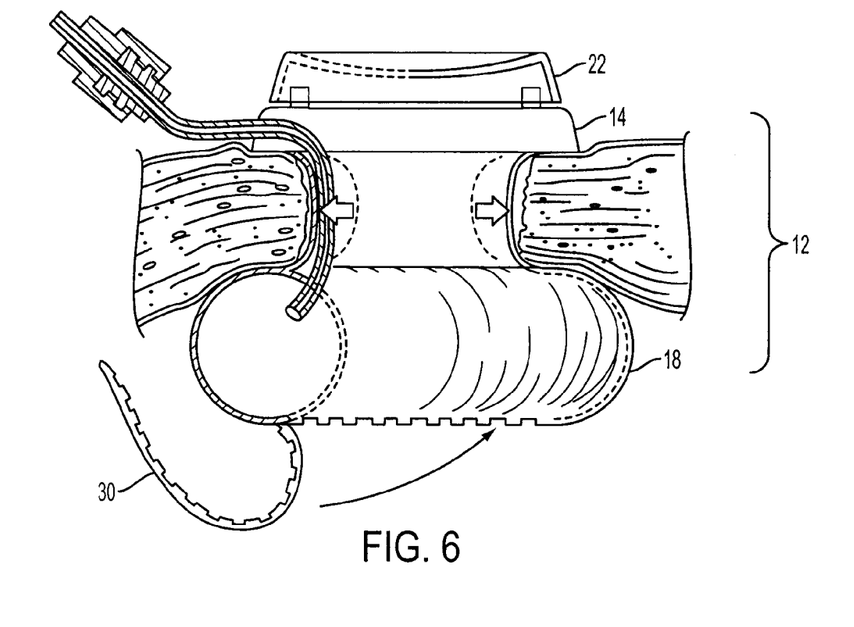
FIG. 6 is a side view of the surgical access device of FIG. 1 showing the inflatable distal portion in an inflated configuration.

The proximal support member 14 can have a variety of configurations, but in the illustrated embodiment the proximal support member 14 is in the form of a circular disc having a distal surface that is configured to rest against the tissue, a proximal surface that is configured to couple to a seal housing, and a side wall extending between the proximal and distal surfaces. The seal housing 22 is configured to removably couple, e.g., using threads or a snap-fit, to the proximal support member 14 to provide various seal elements through which instruments or other devices can be inserted into the proximal support member 14 and into the working channel of the retractor 12. The seal housing 22 can have a variety of configurations, but in the illustrated embodiment the housing 22 can include a distal portion 22d that is configured to removably couple to a proximal portion 14p of the proximal support member 14, a proximal surface 22p that can include one or more openings that extends into ports containing seal elements 24 configured to receive instruments or other devices therethrough, and a side wall 22s extending between the proximal surface 22p and the distal portion 22d. The housing 22 can have any shape and size and it can be rigid or flexible depending on the intended use. The illustrated housing 22 is substantially cylindrical with an inner lumen formed therethrough that can be aligned with an inner lumen of the proximal support member 14 and the central portion 16 of the retractor 12 to allow instruments and other devices to be passed through the housing 22 and into the central portion 16 of the retractor 12, for example, through one or more of the seal elements 24 formed in the proximal surface 22p of the housing 22.

As indicated above, the housing 22 can include a variety of seal elements 24 that are effective to seal the working channel of the housing 22 when no instrument is disposed therein and/or to form a seal around an instrument disposed therethrough. The seal elements 24 can be particularly useful to prevent gases from escaping through the retractor 12 and the housing 22 to maintain the insufflation of the body cavity. Various seals are known in the art, but typically the surgical access device can include at least one instrument seal that forms a seal around an instrument disposed therethrough, but otherwise does not form a seal when no instrument is disposed therethrough; at least one channel seal or zero-closure seal that seals the working channel when no instrument is disposed therethrough; or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc.

The proximal support member 14 can also include an insufflation port 26 formed therein through which the inflatable distal portion 18 of the retractor 12 can be inflated and the body cavity can be insufflated. The insufflation port 26 can be located anywhere on the proximal support member 14, but in the illustrated embodiment the insufflation port 26 is located on the sidewall 14s formed between the proximal and distal surfaces 14p, 14d of the proximal support member 14 and it is in fluid communication with the inflatable distal portion 18. The insufflation port 26 can be in fluid communication with the inflatable distal portion 18 in a variety of ways, but in the illustrated embodiment of FIGS. 1-5, a flexible tube can extend from the insufflation port 26 through the central portion 16 and into the inflatable distal portion 18 such that the insufflation port 26 is in direct fluid communication with the inflatable distal portion 18 to deliver the insufflation gas directly to the inflatable distal portion 18. In other embodiments, a channel or pathway can be formed in the sidewall of the central portion 16 and it can extend between the port 26 and the inflatable distal portion 18. A person skilled in the art will appreciate that any technique or configuration can be used to fluidly connect the insufflation port 26 to the inflatable distal portion 18 of the retractor 12. A person skilled in the art will also appreciate that, while a proximal support member and a seal housing are shown, they need not be included and the retractor 12 can be used alone or with various other housing structures.

The flexible elongate central portion 16 of the retractor 12 is configured to extend distally from the proximal support member 14 and to extend through tissue. The central portion 16 can have a variety of configurations, but in the illustrated embodiment the central portion 16 is in the form of an elongate cylindrical tube defining an inner lumen therethrough and having a proximal end 16p that is coupled to and extends from the proximal support member 14 and a distal end 16d that is coupled to the inflatable distal portion 18 of the retractor 12. The central portion 16 can extend from the proximal support member 14 from a variety of locations and it can be coupled to the proximal support member 14 using various techniques. For example, the proximal end 16p of the central member 16 can be integral with the proximal support member 14, or the proximal end 16p of the central member 16 can be attached to the proximal support member 14 by an adhesive, sealant, or any other attachment mechanism known in the art. The particular length of the central portion 16 of the retractor 12 can vary, but the central portion 16 preferably has a length such that the central portion 16 can extend from the proximal support member 14 through the tissue to form a working channel that provides access into a body cavity with the inflatable distal portion 18 of the retractor 12 extending into the body cavity. The diameter of the central portion 16 can also vary, but preferably the central portion 16 has a diameter such that the inner lumen of the central portion 16 is configured to receive a variety of instruments and/or other devices therethrough. The central portion can be formed from a variety of materials that allow the central portion to be flexible and to be inserted into and extend through tissue to create a working channel through tissue. For example, the central portion 16 can be formed from polypropylene, polyethylene, isoprene, sanoprene, polyurethane, or silicone.

As indicated above, the inflatable distal portion 18 of the retractor 12 can be coupled to or formed on the distal end 16d of the central portion 16. The inflatable distal portion 18 of the retractor 12 is movable between an initial configuration, in which the inflatable distal portion 18 is uninflated and is configured to be passed through an incision in tissue, and an inflated configuration in which the inflatable distal portion 18 is inflated and expanded such that the central portion 16 forms a working channel through the tissue to provide access to a body cavity. The inflatable distal portion 18 can have a variety of configurations, but in the illustrated embodiment it is in the form of an inflatable ring-like or donut-shaped structure having a proximal surface 18p that is coupled to and extends from a distal end 16d of the central portion 16, and a distal surface 18d defining a central opening that is effective to allow instruments or other devices to be inserted therethrough and into the body cavity. The inflatable distal portion 18 can be coupled to the distal end 16d of the central portion 16 in a variety of ways, or the inflatable distal portion 18 can be integrally formed with the central portion 16 or on the distal end 16d thereof. For example, the central portion 16 can be formed from a tubular material and a terminal end of the material can be folded over on itself and sealed to create a donut-shaped balloon. The size of the inflatable distal portion 18 can vary, but it preferably has a size in the initial, uninflated configuration that allows the inflatable distal portion 18 to be passed through an incision in tissue and positioned within the body cavity, and it has a size in the inflated configuration such that the inflatable distal portion 18 is configured to extend beyond the opening formed through tissue on the inner wall of the body cavity to anchor the inflatable distal portion 18 of the retractor 12 in the body cavity. In one embodiment, the size of the inflatable distal portion 18 is preferably greater than a diameter of the central portion 16 such that the inflatable distal portion 18 can engage an inner wall of the body cavity.

In order to insufflate the body cavity as the inflatable distal portion 18 is being inflated and moved into the inflated configuration, the inflatable distal portion 18 can include at least one opening 20 formed therein. Any number of openings 20 can be formed in the inflatable distal portion 18. The openings can be positioned anywhere around the diameter of the inflatable distal portion 18 in any configuration, or they can be located elsewhere on the inflatable distal portion 18. For example, the openings 20 can be evenly spaced around the diameter of the inflatable distal portion 18, or the openings 20 can be positioned at different locations around the diameter of the inflatable distal portion 18. The openings 20 can have any shape, and the size of the openings can vary, but preferably the openings 20 are of a size such that the inflatable distal portion 18 of the retractor 12 remains inflated even as gas is passing through the openings 20 and into the body cavity. In other words, the openings 20 are preferably configured to allow gas to pass therethrough at a rate that is less than a delivery rate of insufflation, which is typically about 10 to 30 liters per minute. A person skilled in the art will appreciate that various other configurations can be used to insufflate the body cavity through the inflatable distal portion 18, including forming the inflatable distal portion from a porous material to allow the insufflation gas to pass therethrough.

The inflatable distal portion 18 can also include features to seal the opening defined by the distal surface 18d of the inflatable distal portion 18 such that the working channel through the retractor 12 is sealed to allow insufflation of a body cavity prior to coupling a seal housing to the retractor 12. Such features can also allow a finger or other device to push the inflatable distal portion 18 and the central portion 16 through an incision in tissue. In one embodiment, a membrane 30 can extend across the opening in the distal surface 18d of the inflatable distal portion 18 to seal the working channel. The membrane 30 can have a variety of configurations. In the embodiment illustrated in FIGS. 3-4, the membrane 30 is formed across the opening in the distal surface 18d of the inflatable distal portion 18 and it is perforated such that insertion of a surgical instrument or any other device through the central portion 16 and the membrane 30 will tear the membrane 30 along the perforations to unseal the working channel. The membrane 30 can be perforated along any portion of the inflatable distal portion 18. For example, the membrane 30 can be perforated around substantially the entire perimeter of the inflatable distal portion 18, with only a portion of the membrane 30 remaining attached to the inflatable distal portion 18 after the membrane 30 is torn to prevent the membrane 30 from falling into the body cavity but still providing an opening through the inflatable distal portion 18 to unseal the working channel. The membrane 30 can also be perforated along the entire perimeter of the inflatable distal portion 18 and a variety of grasping tools can be used to grasp and tear the membrane 30 to unseal the working channel such that the membrane 30 can be removed through the working channel of the retractor 12 as the tool is moved proximally and removed from the working channel after the membrane 30 has been torn.

Figure 11:
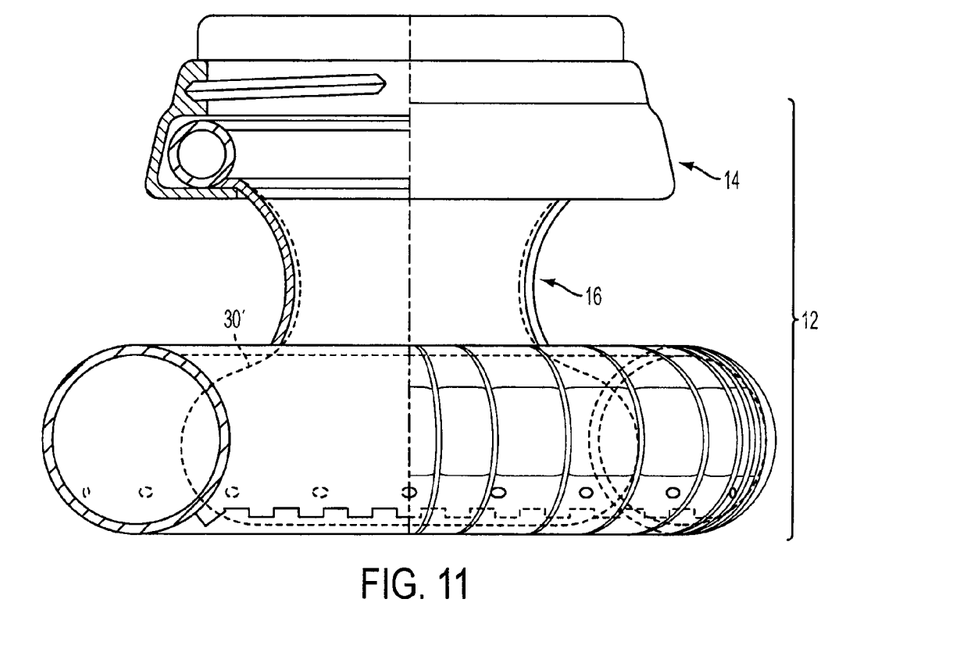
FIG. 11 is a side view of another embodiment of a surgical access device having a membrane extending through an elongate central portion of a retractor.

In other embodiments, the membrane can function to protect the central portion of the elongate member from damage and/or puncturing from instruments or other devices inserted through the working channel formed therethrough. In one embodiment shown in FIG. 11, a membrane 30' can extend from a portion of the proximal support member 14 of the retractor 12 and it can extend through the central portion 16 to protect the retractor 12 from puncture during insertion of instruments therethrough. The membrane 30' can also optionally function to seal the working channel prior to insertion of instrument therethrough. The membrane 30' can have a variety of configurations, but in one embodiment the membrane 30' is in the form of an elongate cylindrical tube defining an inner lumen therethrough and having a proximal end that is coupled to and extends from the proximal support member 14, and optionally a closed distal end for sealing the working channel. The membrane 30' can extend from the proximal support member 14 from a variety of locations and it can be coupled to the proximal support member 14 using any technique known in the art. The length of the membrane 30' can vary, but the membrane 30' preferably has a length such that the membrane 30' can extend from the proximal support member 14 and through the central portion 16. The diameter of the membrane 30' can also vary, but preferably the membrane 30' has a diameter such that the inner lumen of the membrane 30' is less than the diameter of the central portion 16 but large enough to receive a variety of instruments and/or other devices therethrough for tearing the distal end of the membrane 30' to unseal the working channel. The membrane can be semi-rigid to allow the membrane to be inserted through tissue but rigid enough to protect the central portion 16. Similar to membrane 30, the membrane 30' can be perforate around a portion of the distal end of the membrane or around the entire perimeter of the distal end of the membrane 30' such that a tool can tear the distal end of the membrane 30' along the perforations to unseal the working channel. After tearing the of the membrane 30' to open the working channel, the membrane 30' can remain within and extend along an inner surface of the central portion 16 to provide protection to the central portion 16 from tool and instruments being inserted therethrough.

Figure 12:
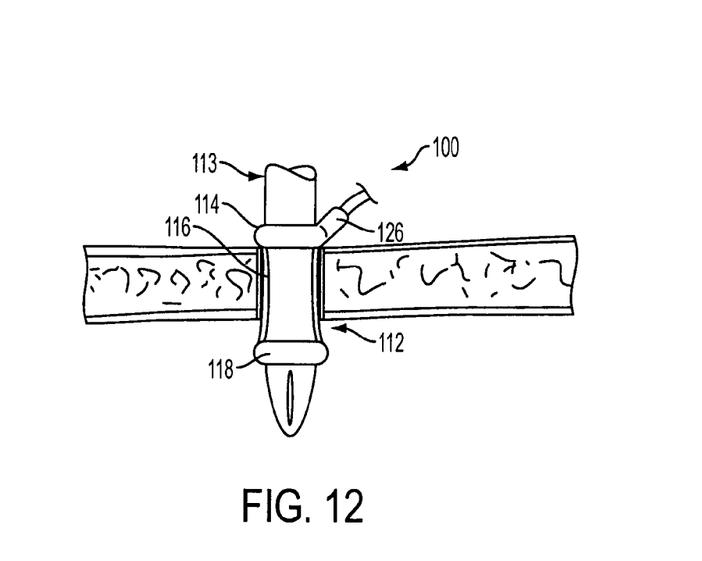
FIG. 12 is a side view of another embodiment of a surgical access device that includes a retractor having inflatable proximal and distal portions and an elongate central portion extending therebetween, showing the inflatable proximal and distal portions in an uninflated configuration.
Figure 13:
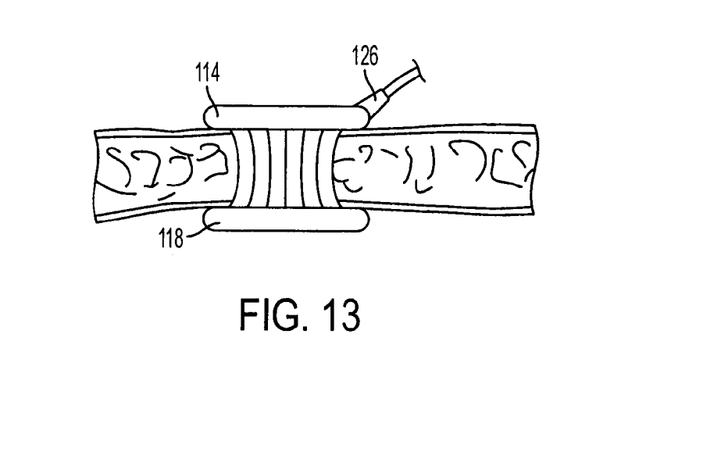
FIG. 13 is a side view of the surgical access device of FIG. 12 showing the inflatable proximal and distal portions in an inflated configuration.

A surgical access device can also be provided that includes inflatable portions at both the proximal and distal ends of a retractor. For example, as shown in FIGS. 12-13, a surgical access device 100 generally includes a retractor 112 having an inflatable proximal portion 114 configured to inflate and rest against an external tissue surface, an inflatable distal portion 118 configured to inflate within the body cavity and rest against an internal tissue surface, and an elongate central portion 116 extending therebetween. The inflatable proximal and distal portions 114, 118 of the retractor 112 are movable between an initial reduced diameter configuration in which the inflatable distal portion 118 is configured to be passed through an incision in tissue, and an inflated configuration in which the inflatable portions 114, 118 are expanded to engage tissue therebetween, and the central portion 116 forms a working channel through the tissue to provide access to a body cavity. In one embodiment, a tool, such as a trocar 113 as shown in FIG. 12, can be used to push the distal portion 118 of the retractor 112 through tissue when the inflatable distal portion 118 is in the uninflated configuration. Insufflation gas can be passed through a port formed on the proximal portion 114 to move the inflatable portions into the inflated configuration, as shown in FIG. 13.

The inflatable proximal portion 114 can have a variety of configurations, but in the illustrated embodiment it is in the form of an inflatable ring-like or donut-shaped structure having a distal surface 114d that is configured to couple to a proximal end 116p of the central portion, and a proximal surface 114p having an opening therethrough for receiving instruments therein. The proximal portion 114 can include an insufflation port 126 formed thereon through which the inflatable portions 114, 118 of the retractor 112 can be inflated and/or the body cavity can be insufflated. The insufflation port 126 can be in fluid communication with the inflatable portions 114, 118 in a variety of ways, but in the illustrated embodiment of FIGS. 12-13, the insufflation port 126 is in fluid communication with the inflatable proximal portion 114, which communicates with the distal portion 118 via the central portion 116 such that the insufflation port 126 can deliver the insufflation gas through the entire retractor 112. For example, a channel or pathway can be formed in the sidewall of the central portion 116 and it can extend between the inflatable proximal portion 114 and the inflatable distal portion 118.

Similar to the central portion 16 described above, the central portion 116 of the retractor 112 is configured to extend distally from the inflatable proximal portion 114 and to extend through tissue. The central portion 116 can have a variety of configurations, but in the illustrated embodiment the central portion 116 is in the form of an elongate cylindrical tube defining an inner lumen therethrough and having a proximal end 116p that is coupled to and extends from the inflatable proximal portion 114 and a distal end 116d that is coupled to the inflatable distal portion 118 of the retractor 112. Similar to the inflatable distal portion 18 described above, the inflatable distal portion 118 can have a variety of configurations, but in the illustrated embodiment it is in the form of an inflatable ring-like or donut-shaped structure having a proximal surface 118p that is coupled to and extends from a distal end 116d of the central portion 116, and a distal surface 118d defining a central opening that is effective to allow instruments or other devices to be inserted therethrough and into the body cavity.

A person skilled in that art will appreciate that any of the features described above with respect to the surgical access device 10 can also be included as a feature of the surgical access device 100. For example, the inflatable distal portion 118 can include a plurality of openings formed therein, similar to the openings 20 in the inflatable distal portion 18, for insufflating the body cavity during inflation of the inflatable distal portion 118. The inflatable distal portion 118 can also include any of the membranes described above for providing a seal through the working channel or protecting the central portion 116 of the retractor 112 during insertion of instruments or other devices through the working channel. A person skilled in the art will also appreciate that the proximal support member 14 of the retractor 12 can optionally include a proximal inflatable portion such as the proximal inflatable portion 114 of the retractor 112.

Figure 7:
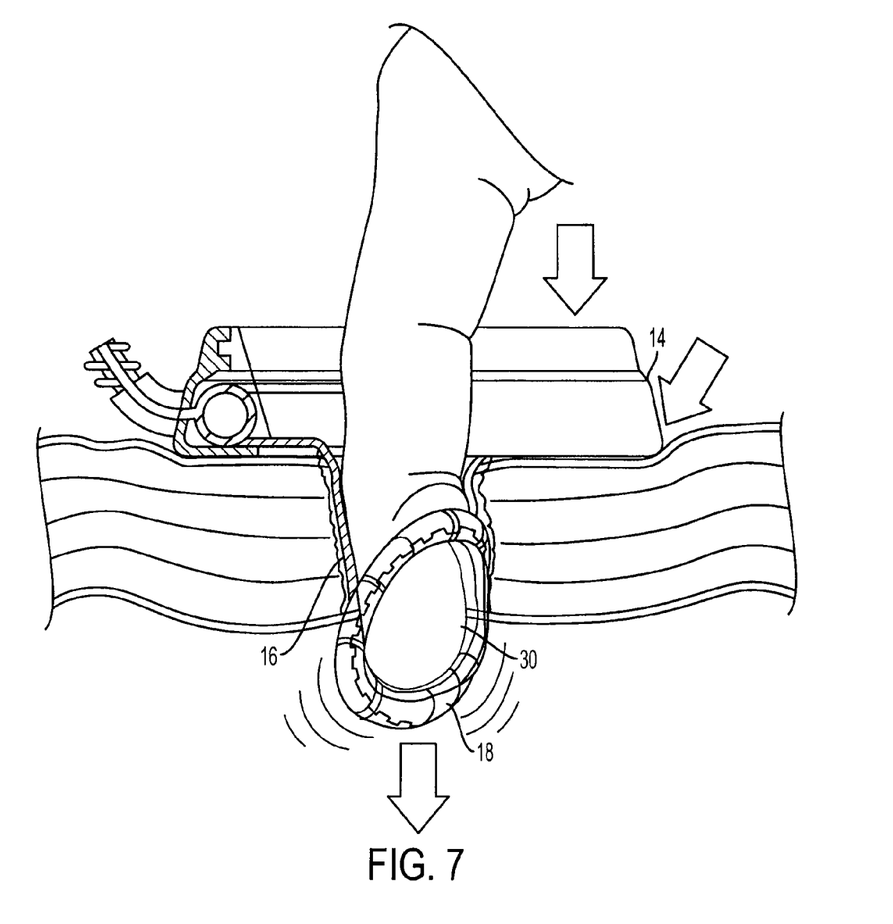
FIG. 7 is a side view of the surgical access device of FIG. 1 showing the proximal support member resting against tissue and the central portion and inflatable distal portion being inserted through tissue.
Figure 8:
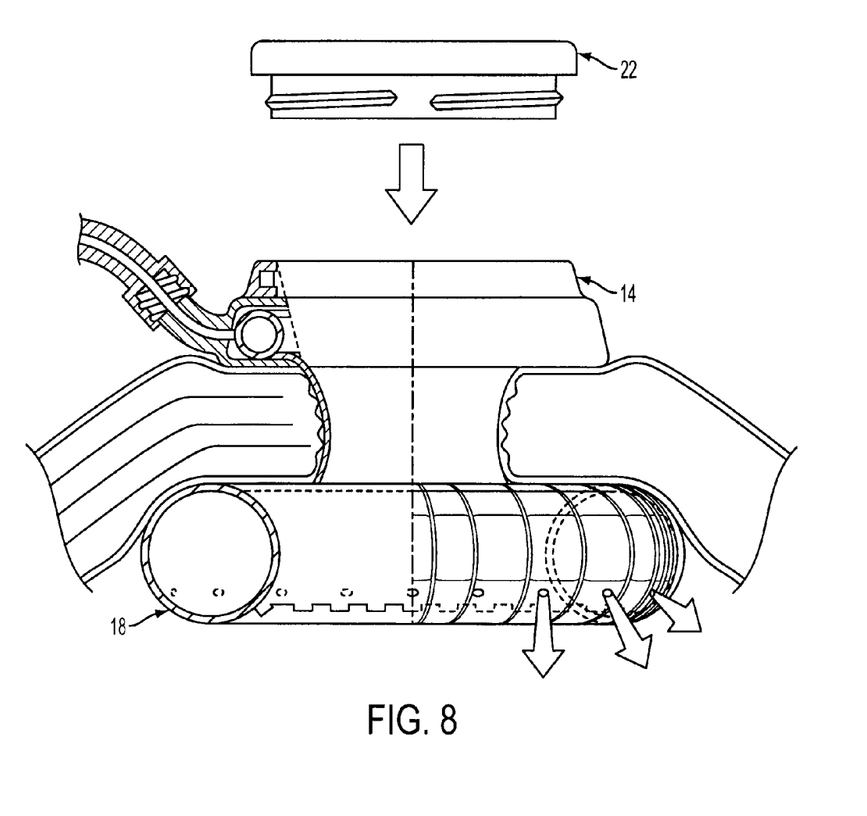
FIG. 8 is a side view of the surgical access device of FIG. 7 showing the inflatable distal portion in the inflated configuration and the seal housing being coupled to the proximal support member.
Figure 9:
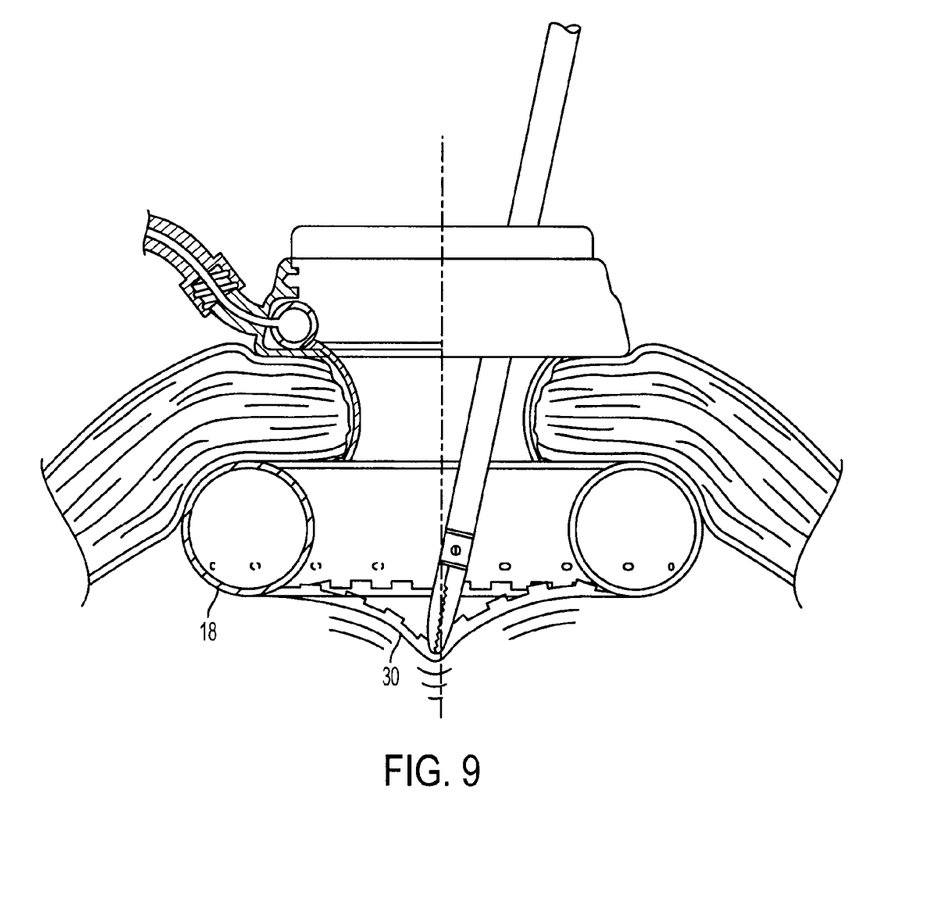
FIG. 9 is a side view of the surgical access device of FIG. 8 showing a tool inserted through the retractor for tearing a membrane disposed across the inflatable distal portion to unseal the working channel.
Figure 10:
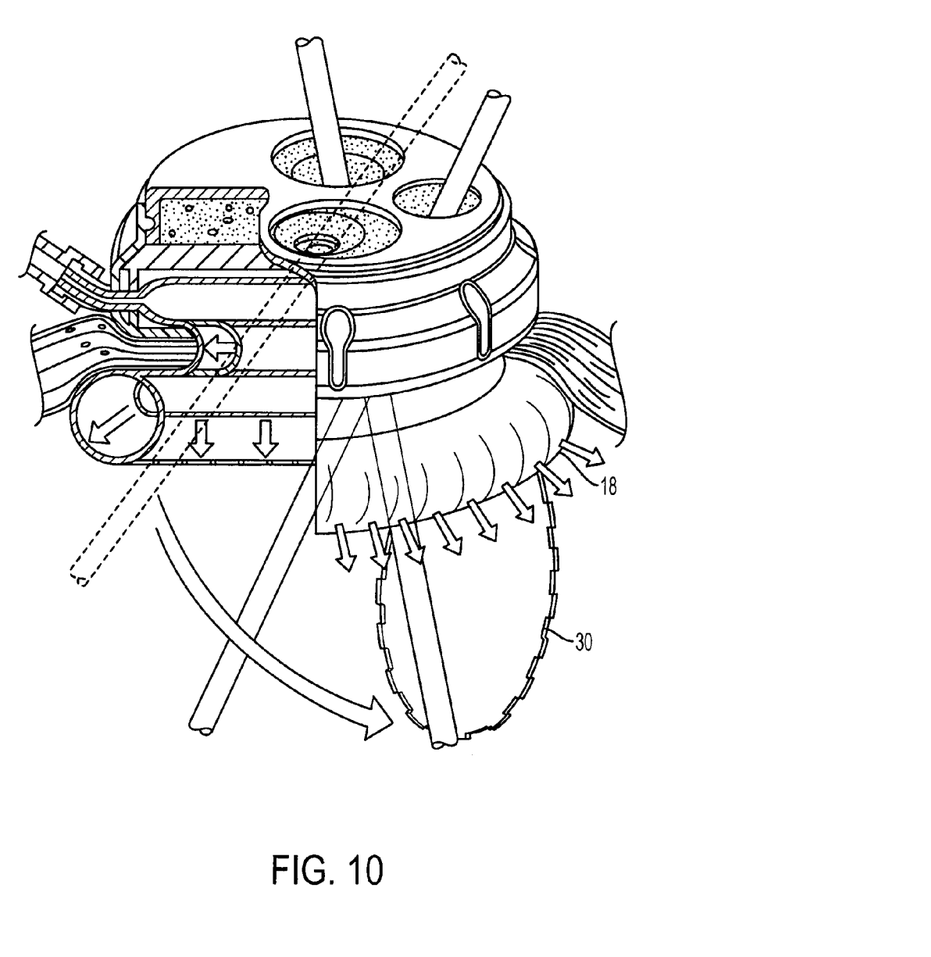
FIG. 10 is a side partial-cross-sectional view of the surgical access device of FIG. 9 showing various tool inserted through seal elements in the seal housing and extending through the working channel and into the body cavity.

A method for accessing a body cavity is also provided herein. In one embodiment, as shown in FIG. 7, a small incision can be made in the skin, and an instrument or fingertip can be inserted through the proximal support member 14 and into the central portion 16. The central portion 16 and the inflatable distal portion 18 can be pushed through tissue with the inflatable distal portion in the uninflated configuration. The proximal support member 14 of the retractor can be positioned to rest on the tissue wall through which the retractor has been inserted, and the inflatable distal portion 18 of the retractor can be positioned within a body cavity, such as in the peritoneal cavity. The inflatable distal portion 18 can then be inflated, as shown in FIG. 8, to move the inflatable distal portion 18 into the inflated configuration such that the inflatable distal portion 18 can extend beyond the opening formed in the wall in the body cavity to engage an inner surface of the tissue wall and thereby anchor the inflatable distal portion within the body cavity. In particular, a gas can be passed through the insufflation port disposed on the proximal support member and delivered to the inflatable distal portion to inflate and expand the inflatable distal portion, while also insufflating the body cavity through one or more openings formed in the inflatable distal portion 18. A seal housing 22 can be removably coupled to the proximal support member, as shown in FIG. 8. The seal housing 22 can be attached at any point during the procedure, but it is preferably attached prior to puncturing the membrane. In order to allow insertion of instruments through the seal housing 22 and retractor, a tool can be passed through one of the seal elements in the seal housing 22 and through the retractor such that the tool can tear at least a portion of the membrane 30 sealing the working channel, as shown in FIG. 9. In one embodiment, the membrane 30 can be torn along perforations formed therein to allow various instruments to be passed through the working channel, as shown in FIG. 10, and into the body cavity. The seal elements in the seal housing 22 will maintain a seal in the working channel to prevent the escape of insufflation.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical access device, comprising:
an elongate member having a working channel extending therethrough between a proximal end and a distal end, the elongate member including
a proximal support member configured to rest against an external tissue surface,
a flexible elongate central portion extending distally from the proximal support member and configured to extend through tissue, and
an inflatable distal portion coupled to a distal end of the central portion, the inflatable distal portion being movable between an initial configuration, in which the inflatable distal portion is configured to be passed through an incision in tissue, and an inflated configuration in which the inflatable distal portion is expanded such that the central portion forms a working channel through the tissue to provide access to a body cavity;
wherein the inflatable distal portion includes at least one opening formed therein such that gas delivered to the inflatable distal portion to move the inflatable distal portion to the inflated position flows through the at least one opening to allow insufflation of a body cavity containing the inflatable distal portion.
2. The surgical access device of claim 1, further comprising a membrane extending across the distal end of the working channel and effective to seal the working channel to allow insufflation of a body cavity during inflation of the inflatable distal portion.

3. The surgical access device of claim 2, wherein the membrane is perforated such that insertion of a surgical instrument through the membrane is configured to tear the membrane along the perforations.

4. The surgical access device of claim 3, wherein the membrane is perforated along a substantial portion of a perimeter thereof.

5. The surgical access device of claim 2, wherein a portion of the membrane extends through the flexible elongate central portion, and wherein the membrane is semi-rigid such that the membrane is configured to protect the flexible elongate central portion from being punctured by a surgical instrument.

6. The surgical access device of claim 1, further comprising a seal housing removably mated to the proximal support member, the seal housing including at least one seal element disposed therein and configured to seal the working channel.

7. The surgical access device of claim 1, wherein the at least one opening in the inflatable distal portion comprises a plurality of openings.

8. The surgical access device of claim 1, wherein the proximal support member includes an insufflation port formed therein and in fluid communication with the inflatable distal portion of the elongate member.

9. The surgical access device of claim 1, wherein the proximal support member and the inflatable distal portion are ring-shaped.

10. The surgical access device of claim 1, wherein the proximal support member includes an inflatable proximal portion being movable between an initial configuration, in which the inflatable proximal portion is configured to be passed through an incision in tissue, and an inflated configuration in which the inflatable proximal portion is expanded such that the central portion forms a working channel through the tissue to provide access to a body cavity.

11. A surgical access device, comprising:
a retractor having a proximal housing configured to rest adjacent an external tissue surface and a flexible member extending therefrom, the retractor having a working channel extending therethrough and configured to form a working channel through tissue, the flexible member including an inflatable portion having at least one opening formed therein; and
an insufflation port formed in the proximal housing and in fluid communication with the inflatable portion such that the insufflation port is configured to deliver an insufflation gas to the inflatable portion of the flexible member to inflate the inflatable portion and to insufflate a body cavity through the openings formed in the inflatable portion.

12. The surgical access device of claim 11, further comprising a puncturable membrane extending across the working channel such that the membrane is configured to be pushed through tissue to position the flexible member of the retractor through the tissue.

13. The surgical access device of claim 12, wherein the membrane is perforated along at least a portion of a perimeter thereof such that insertion of a surgical instrument through the working channel of the retractor is effective separate the membrane from the retractor along the perforations.

14. The surgical access device of claim 11, further comprising a seal housing removably mated to the proximal housing, the seal housing including at least one seal element disposed therein and configured to seal the working channel.

15. The surgical access device of claim 11, wherein the at least one opening in the inflatable portion comprises plurality of openings.

16. A method for accessing a body cavity, comprising:
positioning a proximal support of a surgical access device adjacent to a tissue surface;
inserting a flexible retractor of the access device through an incision in the tissue to position an inflatable portion of the flexible retractor within a body cavity;
delivering an insufflation gas to an insufflation port on the proximal support to inflate the inflatable portion such that a working channel of the access device forms a pathway through the tissue for introducing surgical instruments into the body cavity, wherein the insufflation gas delivered to the inflatable portion flows through at least one opening in the inflatable portion to insufflate the body cavity.

17. The method of claim 16, wherein inserting the flexible retractor through an incision in the tissue comprising applying force to a flexible membrane extending across the working channel to insert the flexible retractor through the incision and to position the inflatable portion within the body cavity, the flexible membrane sealing the working channel of the access device to prevent escape of insufflation gas from the body cavity.

18. The method of claim 17, further comprising coupling a seal housing to the proximal support of the surgical access device, the seal housing having at least one seal element disposed therein that seals the working channel of the access device.

19. The method of claim 18, further comprising inserting a surgical instrument through the seal element in the seal housing and into the body cavity such that the surgical instrument punctures the flexible membrane.

20. The method of claim 19, wherein the flexible membrane prevents contact between the flexible retractor and the surgical instrument.

* * * * *